United States Patent [19]

Farrar

[11] Patent Number: 4,609,755
[45] Date of Patent: Sep. 2, 1986

[54] SYNTHESIS OF VINYL ESTERS

[75] Inventor: David Farrar, West Yorkshire, England

[73] Assignee: Allied Colloids Limited, England

[21] Appl. No.: 723,012

[22] Filed: Apr. 15, 1985

Related U.S. Application Data

[63] Continuation-in-part of Ser. No. 543,734, Oct. 20, 1983.

[30] Foreign Application Priority Data

Apr. 25, 1984 [GB] United Kingdom ............... 8410497

[51] Int. Cl.$^4$ ............................................. C07C 67/02
[52] U.S. Cl. ..................................... 560/217; 556/54; 556/181
[58] Field of Search ................... 560/217; 556/54, 181

[56] References Cited

U.S. PATENT DOCUMENTS 4,333,881  6/1982  Greco et al. ........................... 556/54
4,543,422  9/1985  Farrar ................................. 560/217

OTHER PUBLICATIONS

Kaiser, Emil et al., *J. Am. Chem. Society*, vol. 78 (1956), pp. 3841-3843.

*Primary Examiner*—Natalie Trousof
*Assistant Examiner*—L. Hendriksen
*Attorney, Agent, or Firm*—Lawrence Rosen

[57] ABSTRACT

An ester interchange process, preferably for the formation of vinyl higher esters from methyl acrylate or methacrylate, is conducted in the presence of a novel alcoholate of the formula $$[M^1(OR^4)_{2-a}R_a^6]_x[M^2(OR^4)_{n-b}R_b^6]_y \qquad I$$

wherein
$M^1$ is selected from Mg, Ca and Ba
$M^2$ is selected from Ti, Zr and Al
n is 3 or 4 and is the valency of $M^2$
a is a number from 0 to 1.5
b is a number from 0 to 0.75n
x+Y=1 and each is a number from 0.005 to 0.995 and is such that the compound is liquid at 30°0 C.
$R^4$ is selected from alkyl having at least 4 carbon atoms, cycloalkyl having at least 4 carbon atoms and aminoalkyl, and
each group $R^6$ is individually selected from $C_{1-3}$ alkoxy and blocking groups that are substantially less reactive in the ester interchange reaction than the groups $OR^4$.

10 Claims, No Drawings

SYNTHESIS OF VINYL ESTERS

This application is a continuation-in-part of U.S. Ser. No. 543,734 filed Oct. 20, 1983.

It is known to be able to make esters of carboxylic acids by an ester interchange reaction according to the reaction scheme $$RCOOR^1 + R^2OH \rightleftharpoons RCOOR^2 + R^1OH$$

In this, typically R is an aliphatic or aromatic group, $R^1$ is a methyl or ethyl group and $R^2$ is an aliphatic group containing more carbon atoms than $R^1$. A catalyst is generally used in order to promote the desired exchange reaction. Various metal alcoholates have been proposed for use as the catalyst. It is however also known to provide the alcohol $R^2OH$ for the reaction in the form of a metal alcoholate instead of using alcohol and catalyst. Thus in JACS 78, page 3841 Kaiser et al describe, for example, the reaction of tosylglycine methyl ester with aluminium isopropoxide to form aluminium methoxide and tosylglycine isopropyl ester.

It is recognised that it is difficult to achieve a good conversion in this reaction and Kaiser et al describe ways of improving the conversion. In one method, they conduct the reaction in the presence of a solvent for the starting aluminium alcoholate and in practice they use alcohol as this solvent. In another process, they add the alcohol of the starting aluminium alcoholate (e.g. isopropanol) to the reaction mixture in order to convert the aluminium alcoholate formed during the reaction (e.g. aluminium methoxide) back to aluminium isopropoxide in the reaction mixture.

Particular problems arise in ester interchange reactions that are conducted starting from a vinyl ester such as methyl acrylate or methyl methacrylate. Although ester interchange does occur, in most processes it is accompanied by the formation of undesirable by-products, due especially to addition across the double bond of the vinyl group. Much research has therefore been conducted into developing processes that give a minimum of condensation across the double bond and a maximum of ester interchange. The problem is particularly acute in the synthesis of dialkylaminoalkyl acrylates and methacrylates starting from acrylic or methacrylic lower alkyl ester and a dialkylamino alcohol. The end products are very valuable, for instance for the formation of cationic polymers, and ester interchange is generally the preferred synthesis since starting from, for instance, acrylic acid or acryloyl chloride incurs various disadvantages.

In U.S. Pat. No. 2,138,763, various amino alcohols are reacted with methyl methacrylate in the presence of an alkali metal alcoholate ester interchange catalyst, generally a small amount of sodium methoxide. In Examples 6 and 7, methacryloylchloride is reacted with the sodium alcoholate of the chosen amino alcohol. However, the use of methacryloylchloride is unsatisfactory on a commercial scale, for instance because of difficulties of handling it.

In Japanese Application No. 71748/73 (Kokai 7519716), it is proposed to conduct the ester interchange between an amino alcohol and methyl or ethyl acrylate or methacrylate in the presence of a catalytic amount of a magnesium alcoholate, generally formed from the starting alcohol. It is emphasised that the amount of catalyst should be not more than 10% and the amount used in the examples is 3%. Other processes that have been described include, for example, Japanese Kokai 75142513, in which a calcium compound is used as catalyst, U.S. Pat. No. 4,059,617 in which a phenoxide is used as a catalyst, Japanese Kokai 77153991 in which a lithium or a sodium compound is used as catalyst, and British Pat. Nos. 1 572 438 and 1 556 310 in which tin compounds are used as catalysts. Although the use of a metal alcoholate as a reactant rather than as a catalyst is known for the production of other esters (see the article by Kaiser et al), generally in the presence of free alcohol, this process has never been proposed in the context of vinyl esters presumably because of the known probability of poor yields or undesirable side reactions.

It has become accepted that the best way of effecting ester interchange for vinyl esters is by reaction of the vinyl lower alkyl ester with the chosen alcohol in the presence of a catalyst. The catalyst is generally a titanium alcoholate or aluminium alcoholate but, as is apparent from the literature quoted above, there have been numerous proposals to use sodium or other alcoholates. Although these processes are used widely, they are not entirely satisfactory. It is difficult to obtain good yields of pure products and in particular, formation of undesirable byproducts is difficult to avoid. The process involves the formation of azeotropes between alcohol and ester and it is difficult to separate these azeotropes into their components.

We have now surprisingly found that it is possible to achieve high yields of pure product, in the substantial absence of impurities, by reaction of a vinyl lower alkyl ester with an appropriate metal alcoholate provided the metal is selected from a narrow group of metals and provided the reaction is conducted in the substantial absence of any water or reactive alcohol.

In particular, in the invention we make an ester of the formula $R^3COOR^4$ where $R^3$ is $CH_2\!=\!CH\!-$ or $CH_2\!=\!C(CH_3)\!-$ and $R^4$ contains at least four carbon atoms and is selected from alkyl, cycloalkyl and aminoalkyl by reaction of a compound of the formula $R^3COOR^1$, where $R^1$ is $C_{1-3}$ alkyl, in the presence of a metal alcoholate formed from an alcohol $R^4OH$ and in this process, the metal alcoholate provides the groups $R^4$ that are utilised in forming the desired ester and reacts with the compound $R^3COOR^1$, the reaction is conducted in the substantial absence of water or reactive alcohol and metal is selected from titanium, aluminium, zirconium, calcium and magnesium.

An important feature of the invention relates to the use of this process for forming aminoalkyl esters, since the difficulties of ester interchange are particularly serious with these and the process of the invention is especially effective for the formation of such esters. The alkyl group of the aminoalkyl radical generally contains at least two carbon atoms and the aminoalkyl group is generally a dialkyl aminoalkyl group. Preferably it is a group of the formula $(R^5)_2N-C_nH_{2n}$, where n is two or three and the groups $R^5$, which may be the same or different, are $C_{1-3}$ alkyl. The process is of particular value when the aminoalkyl group is dimethylaminoethyl. The metal may be zirconium but is often titanium, aluminium, calcium or magnesium and, as discussed below, best results are generally achieved with calcium or magnesium.

The aminoalkyl esters are known compounds and are useful for forming known polymers that are of value as, for instance, flocculants. The process is, however, also applicable to the production of alkyl and cycloalkyl esters having more than four, and generally more than five, carbon atoms. Cycloalkyl esters generally contain five to eight carbon atoms. Preferably, however, the esters are alkyl esters containing from five to thirty carbon atoms. The long chain esters, for instance containing fifteen to thirty carbon atoms and preferably twenty to twenty four, typically around twenty two, carbon atoms are of particular value in the production of polymers for use as suspension stabilisers while the cycloalkyl and shorter chain length alkyl esters, for instance containing six to fifteen and generally seven to ten, typically around eight, carbon atoms, are of value as pour point depressants. They are all known compounds.

It has normally been assumed, in ester interchange reactions, to be desirable to have any metal alcoholate in solution in the reaction mixture, i.e. the mixture should be homogeneous. An important feature of the invention is that we have found that in the particular ester interchange process of the invention, it is often very advantageous that the starting metal alcoholate should be insoluble in the reaction mixture. The reaction is generally conducted in the absence of any solvent and so whether or not the alcoholate is soluble in the mixture will depend on the metal, the alcohol used for forming the alcoholate, and the starting ester. In practice, the alcoholates of calcium and magnesium are generally insoluble and particularly good results are achieved when $R^4$ represents aminoalkyl, as discussed above, and the metal is selected from calcium and magnesium. By saying that the alcoholate is insoluble, we mean that its solubility is so low that the great majority is insoluble, for instance, its solubility is below 5% and generally below 1% in the reaction mixture.

An important feature of the invention is that, as a result of utilising defined materials in the absence of free alcohol, it is possible to operate the process commercially in a particularly effective manner so as to obtain maximum yields with minimum consumption of reactants. An important feature of preferred processes of the invention is that the metal alcoholate formed in the reaction should be removed from the reaction mixture and should then be reacted with excess alcohol $R^4OH$ and the resultant metal alcoholate is then recycled to the reaction mixture. Thus this reaction with alcohol $R^4OH$ must occur in the substantial absence of the ester $R^3COOR^1$ and so, by this process, one achieves not only substantially total reuse of the metal but also avoids the formation of azeotropes between the starting ester and the alcohol.

The preferred process of the invention involves carrying out the following sequential steps. In step A, the ester interchange reaction is conducted between the metal alcoholate formed from the alcohol $R^4OH$ and an excess of the ester $R^3COOR^1$ to form a mixture containing the ester $R^3COOR^4$, unreacted ester $R^3COOR^1$ and metal alcoholate that has at least partially been converted to an alcoholate formed from the alcohol $R^1OH$. In step B, this alcoholate is separated from the reaction mixture, the ester $R^3COOR^4$ is recovered from the reaction mixture and the ester $R^3COOR^1$ is recycled for use in step A. In step C, the separated alcoholate from step B is reacted, in the substantial absence of ester $R^3COOR^1$, with excess alcohol $R^4OH$ to form alcohol $R^1OH$ and alcoholate formed from the alcohol $R^4OH$. In step D, this alcoholate, formed in step C, is separated and recycled for use in step A and the alcohol $R^4OH$ is recovered and recycled for use in step C. The alcohol $R^1OH$ is taken off as an end product.

Generally step B is effected by separating the alcoholate from the esters followed by separating the esters by fractional distillation, while step C is effected by separating the alcoholate from the alcohols followed by separating the alcohols by fractional distillation. When the alcoholate in a mixture, is insoluble in that mixture separation can be by filtration (for instance centrifugation) but if the alcoholate is soluble, separation can be by evaporation of the more volatile organic component from the less volatile metal alcoholate. In order to avoid prolonged heating, this evaporation is preferably by flash evaporation.

The starting ester is generally methyl acrylate or methacrylate or ethyl acrylate or methacrylate. The starting metal alcoholate may be formed only from the alcohol $R^4OH$ in which event the metal alcoholate has the formula $M(OR^4)_m$ where M is the metal and m is the valency of the metal, but in some instances it is desirable for some, but not all, of the valencies of the metal M to be blocked by an inert group $R^6$ so that the metal alcoholate then has the formula $M(OR^4)_{m-n}(R^6)_n$ where n is a number less than m and is generally 1. $R^6$ is any group that is substantially less reactive in the ester interchange reaction than the group $OR^4$, with the result that it will remain attached to the metal M during the reaction. It is normally an alkyl or alkoxy group containing eight to thirty carbon atoms but, if it is an alkoxy group, it is generally essential for it to contain more carbon atoms than $R^4$ as otherwise it may enter into the reaction. A preferred blocking group $R^6$ is stearyl. The inclusion of a blocking group reduces the risk of the metal entering into unwanted side reactions and is generally of interest only when the metal is titanium. Another effective way of minimising the risk of unwanted side reactions when the metal is titanium is to use it as a blend with zirconium. Other blends of metals may also be used in the invention.

It is essential in the invention to use one or more of the named five metals since the use of alcoholates formed with other metals does not give satisfactory results. For instance, the use of sodium or barium alcoholates leads to high byproduct formation, primarily due to addition across the double bond, while the use of other metal alcoholates leads to little or no reaction occurring. The desired alcoholate may be prepared by addition of the chosen metal to the chosen alcohol.

The reaction is preferably conducted using an excess of the starting ester, for example 1.0 to 10 moles of ester per mol of alcoholate. The reaction mixture should be free of the starting alcohol or of any other alcohol that could react under the prevailing process conditions, and is generally free of any alcohol. The reaction mixture should be substantially anhydrous. Very small amounts of water or alcohol may be tolerated but even these may lead to some by-product formation.

The reaction may be carried out simply by mixing the starting ester with the chosen alcoholate. With the preferred alcoholates, of calcium or magnesium, no heating is necessary and the reaction proceeds satisfactorily at ambient temperature, but in general temperatures between 10° and 50° C. can be used. With the titanium, zirconium and aluminium alcoholates, the reaction may proceed at ambient temperatures but it is generally desirable to heat the mixture, for instance to reflux, often at temperatures of 70° to 95° C. The reaction is generally conducted under atmospheric pressure.

The reaction proceeds to an equilibrium position. The time required to reach this depends on the temperature but is generally 10 minutes to 3 hours. For instance, calcium or magnesium alcoholates reacted at ambient temperatures may require 30 to 75 minutes, or less at higher temperatures, while aluminium or titanium alcoholates may require 1 to 2 hours at reflux. The equilibrium may be represented schematically by the equation:

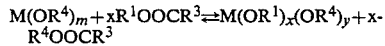

wherein $x+y=m$ and x and y are generally both above 0, usually above 0.1, preferably 0.5 to 2. For simplicity, we have not shown in this reaction scheme the possibility of the use of blocking groups $R^6$, but of course they can be present as well.

The reaction is generally allowed to proceed substantially to the equilibrium position although it is not essential to attain final equilibrium. The desired ester may be recovered from the reaction mix continuously during the reaction or at any time during the reaction or the reaction may be conducted batchwise with the ester being separated at the end of each batch. The desired ester may be recovered in any convenient way, for example by distillation or by centrifugation or other filtration method of removing solid alcoholate, but preferably is removed as part of the cyclic process described above. The alcoholate can be removed, for instance by filtration, either continuously or batchwise. The mixed alcoholates recovered from the reaction mixture will often contain approximately one third to one half of the initial amount of alcohol $R^4OH$ (introduced as alcoholate) and it is therefore desirable to reuse this aminoalcohol. For this purpose, the mixture of alcoholates is converted back to the starting materials. This can be done by reaction of the mixed alcoholate with excess dialkylamino alcohol in accordance with the reaction scheme

Reactant regenerated in this way has proved as effective as material prepared initially from the alcohol $R^4OH$ and the chosen metal.

The following are some examples. Example 1 is an example of a conventional catalytic process such as is conventionally used commercially. Example 2 describes the preparation of a starting alcoholate for use in the invention. Examples 3 to 8 and 10 are examples of the invention and Example 9 is comparative.

EXAMPLE 1

2.5 moles of methyl acrylate and 1.5 moles of DMAE (dimethylamino ethanol) were charged into a reaction vessel. Ti(DMAE)$_4$ to 11.4% by weight of the alcohol was added as catalyst. The mixture was heated to boiling point and methanol/methyl acrylate azeotrope was removed. The pot temperature was initially 89° C. and increased to 166° C. on reaction completion. The percentage of high-boilers (by-products) based on DMAEA was determined as the reaction proceeded. After 200 minutes and 66.5% conversion of DMAE to DMAEA, the percentage was 2.2% (by weight), while after 350 minutes and almost complete conversion the percentage was 8.2%.

EXAMPLE 2

Turnings of magnesium were added in portions to at least one mole excess of dimethylamino ethanol at 130° C. A crystal of iodine is useful in starting the reaction. Heating was continued until most of the metal had reacted (this may take several days). The mixture was then cooled and the dimethylamino ethanol decanted off. The precipitate was then stripped under 10 mm Hg vacuum in an oil bath at 140° C. until no more dimethylamino ethanol could be removed. The other alcoholates used in the examples were made in similar manner or by conversion of lower alkyl alcoholates of the chosen metal.

EXAMPLE 3

Calcium or magnesium alcoholate prepared as in Example 2 was placed in a flask. Methyl acrylate was added to give a mole ratio of 5 moles of acrylate to 1.5 moles of metal alcoholate. A heterogeneous mixture was formed since the methyl acrylate did not dissolve the solid alcoholate. Solubility tests at room temperature showed that the calcium alcoholate dissolved in an amount less than 0.1 in the reaction mixture and the magnesium alcoholate dissolved in an amount of less than 0.6%.

The reaction proceeded at 25° C. and the amount of dimethylamino ethyl acrylate (DMAEA), expressed as a molar percentage based on the amount of alcohol in the alcoholate introduced into the reaction vessel, was determined at various times during the reaction. After 60 minutes, the mixture was centrifuged to remove the solid alcoholates and the liquid phase fractionally distilled to remove the methyl acrylate. The residue, of DMAEA, was analysed and was found to be free of high boiling or other by-products. The results are given in Table 1. Reaction beyond 60 minutes was found, in other experiments, to give no significant change in conversion.

TABLE 1

| Reaction time (mins) | % DMAEA | |
|---|---|---|
| | Mg alcoholate | Ca alcoholate |
| 10 | 12.5 | 10.0 |
| 20 | 17.0 | 15.5 |
| 30 | 19.5 | 18.0 |
| 40 | 21.6 | 19.5 |
| 60 | 24.6 | 20.5 |

EXAMPLE 4

The process of Example 3 was repeated, with heating, using aluminium or titanium alcoholate instead of calcium or magnesium alcoholate.

When the temperature was at reflux (at about 85° C.), reaction started and continued to equilibrium as the reflux temperature rose to 92° C. over a total period of 1.5 hours. Reaction beyond this time gave no significant change in conversion. The results of GLC analysis for DMAEA are shown in Table 2.

TABLE 2

| Reaction time (mins) | % DMAEA | |
|---|---|---|
| | Al alcoholate | Ti alcoholate |
| 10 | 4.7 | 27.4 |
| 20 | 10.0 | 29.7 |
| 30 | 16.5 | 30.5 |
| 35 | 25.5 | 30.7 |
| 60 | 28.0 | 30.8 |
| 90 | 28.7 | 30.8 |

EXAMPLE 5

Methyl methacrylate (1 mole) was reacted with the Mg or Ca alcoholates of dimethylamino ethanol (0.3 moles) at 25° C. The amount of dimethylamino ethylmethacrylate (DMAEMA) formed at various times during the reaction was determined and the results are given in Table 3. When the reaction mixtures were allowed to stand, no high boiling impurities were apparent after 24 hours at room temperature in either reaction mixture and there was no significant change in conversion after 60 minutes.

TABLE 3

| Reaction time (mins) | % DMAEMA | |
|---|---|---|
| | Mg alcoholate | Ca alcoholate |
| 10 | 5.8 | 8.0 |
| 20 | 11.1 | 14.3 |
| 35 | 16.1 | 15.9 |
| 45 | 18.4 | 18.4 |
| 60 | 21.8 | 21.8 |

EXAMPLE 6

62.5 g of zirconium tetra dimethylamino ethoxide and 187.5 g of titanium tetra dimethylamino ethoxide were mixed with 349.7 g methyl acrylate and 0.6 g phenothiazine to give a 5:3 molar methyl acrylate to dimethylaminoethanol ratio.

The resultant mass was heated to a temperature such that the methyl acrylate reached reflux temperature. After sixty minutes, the reaction had reached equilibrium giving 23.6% DMAEA. The volatile components were removed by flash evaporation and the resultant liquid was analysed as $Zr_{0.231}Ti_{0.769}(OMe)_{1.65}(DMAE)_{2.35}$. $OMe = OCH_3$: $ODMAE = OCH_2CH_2N(CH_3)_2$

EXAMPLE 7

443 g zirconium tetra dimethylamino ethoxide and 103.2 g methyl acrylate were mixed together and 0.1 g phenothiazine added. The resultant mix was then heated with stirring until the methyl acrylate reached reflux temperature. After 40 minutes, the reaction contained 20.0% by weight DMAEA.

EXAMPLE 8

5 mole equivalents of methyl acrylate were reacted with 1 mole equivalent $Ti(DMAE)_4$ at 80° C. Once reaction equilibrium was attained, after 60 minutes, the volatiles were removed by rapid distillation at 120° C. and 20 mm Hg pressure and DMAEA was separated. Some equilibrium reversal occurred due to slight fractionation under these conditions. The resultant titanium alkoxide was regenerated by the addition of 1–2 moles dimethylaminoethanol per mole of methoxide ligand. Methanol and DMAE were removed slowly by distillation on a rotary evaporator and the residue was recycled for use in the main reaction. The process was repeated 15 times. Table 4 gives the time to equilibrium in each main reaction and the analysis of the titanium alkoxide that had been made in the previous cycle and that had been converted for use in that main reaction.

TABLE 4

| Recycle | $Ti(OCH_3)_x(ODMAE)_{4-x}$ x = | Time to equilibrium (minutes) |
|---|---|---|
| 1 | 1.71 | 70 |
| 2 | 1.49 | 70 |
| 3 | 1.53 | 70 |
| 4 | 1.44 | 60 |
| 5 | 1.39 | 80 |
| 6 | 1.32 | 60 |
| 7 | 1.51 | 60 |
| 8 | 1.46 | 60 |
| 9 | 1.60 | 40 |
| 10 | 1.32 | 40 |
| 11 | 1.62 | 60 |
| 12 | 1.43 | 40 |
| 13 | 1.66 | 60 |
| 14 | 1.36 | 50 |
| 15 | 1.47 | 60 |

It will be seen that the recycled alkoxide maintains its effectiveness.

EXAMPLE 9

When the process of Example 3 was attempted using the corresponding sodium alcoholate reaction occurred exothermically and resulted in very high levels of by-products being formed whether the reactor was cooled or not. Similar results were obtained when the sodium alcoholate was replaced with potassium, lithium or barium alcoholates.

EXAMPLE 10

1170 g titanium tetra isopropanate and 2142 g 2-ethyl hexanol were heated together in a stirred reactor equipped with a fractionation column and reflux splitter. Isopropanol was removed at the top of the column and the pot temperature progressively increased to 160° C., at which point vacuum was progressively applied to remove the last traces of the isopropanol. 930 g isopropanol (94% theory) was recovered although there was some loss down the vaccuum line. 14 g 2-ethyl hexanol was removed from the column bottom once the vacuum was released. The reactor contained 2283 g tetra (2-ethyl hexyl) titanate in the form of a mobile amber liquid with no sign of precipitate.

The metal alcoholate was then stripped on a rotary-evaporator at 140° C. and 10 mm Hg pressure to remove any residual volatiles.

423 g (5 moles) methyl acrylate and 423 g (0.75 moles) of the tetra (2-ethyl hexyl) titanate (as prepared above) were charged into a glass reactor equipped with stirrer and reflux condenser. The reaction mass was heated until the methyl acrylate reached reflux temperature. The extent of reaction was followed by GLC analysis. The reaction mass contained 27.2% w/w 2-ethyl hexyl acrylate after 5 minutes and 47.6% after 15 minutes. Reaction for a further 45 minutes showed no further increase in product and did not lead to formation of impurities.

In the processes described above, those processes in which the metal of the alcoholate is magnesium or calcium can be operated at relatively low temperatures, for instance 10° to 50° C., to give good yields of the desired product. However these metal alcoholates are solids that are insoluble in the reaction mixture and in practice, they can tend to result in the formation of a semi-colloidal mixture having physical characteristics such that separation, further reaction and recycling of the metal alcoholates can give some difficulties in commercial practice.

Alcoholates in which the metal is titanium, aluminium or zirconium have the advantage that they are liquids that are miscible with the reaction mixture and so the handling difficulties are avoided. However, they are less reactive with the result that the process must be conducted at elevated temperatures, generally above 70° C., and even at such temperatures, the rate of reaction may not be as fast as can be achieved at much lower temperatures using, for instance, the magnesium alcoholate. Also the use of elevated temperatures is undesirable both for economic reasons and, in the context of production of vinyl esters, because of the tendency to promote the formation of unwanted polymers. For instance, during prolonged operation the viscosity of the reaction mixture may gradually increase due to the formation of polymeric products. These may include polymerised vinyl ester and may include polymers containing the metal, especially when the metal includes aluminium. When the metal of the alcoholate consists solely of titanium, there may be a tendency for inorganic cross-linked products based on aluminium to be formed during the process.

Somewhat similar difficulties can also be encountered when the metal alcoholate is being used as a catalyst for an ester interchange reaction conducted in the presence of reactive alcohol.

We have now discovered that certain novel metal alcoholates are of particular value in ester interchange reactions, especially for the production of vinyl esters. These metal alcoholates contain at least two metals and are liquid at 30° C. and are miscible with the esters that participate in the ester interchange reaction.

It is known from British Patent Specification No. 1,573,071 to use a chelate of beta-diketone with zirconium or calcium and the use of a mixture of such chelates is exemplified. Usually, however, the catalyst is a metal alcoholate and it has been proposed to form the alcoholate from the alcohol that is to be reacted in the ester interchange reaction. When the ester is unsaturated, the prior art processes often lead to the formation of impurities and may involve difficult separation procedures.

The novel alcoholates have the formula $$[M^1(OR^4)_{2-a}R_a^7]_x[M^2(OR^4)_{n-b}R_b^7]_y \qquad \text{I}$$

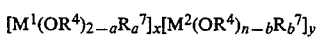

wherein
- $M^1$ is selected from Mg, Ca and Ba
- $M^2$ is selected from Ti, Zr and Al
- n is 3 or 4 and is the valency of $M^2$
- a is a number from 0 to B 1.5
- b is a number from 0 to 0.75n
- $x+y=1$ and each is a number from 0.005 to 0.995 and is such that the compound is liquid at 30° C.
- $R^4$ is selected from alkyl having at least 4 carbon atoms, cycloalkyl having at least 4 carbon atoms and aminoalkyl, and each group $R^7$ is individually selected from $C_{1-3}$ alkoxy and blocking groups that are substantially less reactive in the ester interchange reaction than the groups $OR^4$.

Any blocking groups will normally be a longer chain alkoxy group or will be a hydrocarbon group. Preferred blocking groups are $C_{8-30}$ alkoxy groups and alkyl groups, often $C_{8-30}$ alkyl. The preferred blocking group is $C_{18}$ alkoxide.

The alcoholate may include two or more different groups $R^7$, for instance it may include both blocking groups and $C_{1-3}$ alkoxy groups, but the catalyst before use is preferably free of $C_{1-3}$ alkoxy groups and either contains no groups $R^7$ (a and b are both zero) or contains blocking groups (generally a and b are each up to 1). The catalyst generally includes only one group $R^4$ since if it contains different groups $R^4$, it will result in the production of mixed esters.

$R^4$ is generally cycloalkyl of 5 to 8 carbon atoms, alkyl of 5 to 30 carbon atoms or, preferably, aminoalkyl. When $R^4$ is a long chain alkyl, it often contains 15 to 30 carbon atoms, preferably 20 to 24 carbon atoms. When $R^4$ is a shorter chain alkyl, it is often 6 to 15 and generally 7 to 10 carbon atoms. Preferably $R^4$ is an aminoalkyl group and the alkyl group of the amino alkyl radical generally contains at least 2 carbon atoms and the radical is preferably a dialkyl aminoalkyl group of the formula $(R^5)_2N-C_nH_{2n}$, where n is two or three and the groups $R^5$, which may be the same or different, are $C_{1-3}$ alkyl. Preferably the aminoalkyl group is dimethylaminoethyl.

The values of x and y must be selected such that the catalyst is liquid at 30° C. Generally x is below about 0.5 and often is below about 0.3. Generally it is above 0.01. Best results are generally obtained when x is from about 0.02 to about 0.1 or 0.2. If a catalyst is formed that is solid, then it is generally necessary to modify it by reducing the value of x. For instance, when $M^1$ is Ca or Ba it is often desirable for x to be below about 0.1 or 0.2.

Although the novel alcoholate has been shown above as having an empirical formula consisting of two components, component X being formed from the divalent metal and component Y being formed from the trivalent or tetravalent metal, it should be appreciated that this representation of the alcoholate is used for simplicity and that the precise structural relationship between the groups is at present not entirely clear.

The alcoholate may be a simple physical mixture of components X and Y or it may be a chemical combination. For instance it may be a mixture of, e.g. titanium alcoholate and magnesium alcoholate. The alcoholate can be made by conventional methods for the production of metal alcoholates modified by the use of a mixture of metals, rather than a single metal. For instance, an alcohol $R^4OH$ may be reacted with an appropriate mixture of metals $M^1$ and $M^2$ or may be reacted independently with each of the metals and the two reaction products then combined. Compounds of metals $M^1$ and/or $M^2$ may be used in place of the metals. The preferred method of making the alcoholate is by an alcohol interchange reaction as a result of reaction of an alcohol $R^4OH$ with a $C_{1-3}$ alkoxide either of a mixture of the metals $M^1$ and $M^2$ or of the individual metals $M^1$ and $M^2$ followed by combination of the resultant alcoholate. Generally the reaction is taken to completion as a result of which the final product will be free of lower alkoxy groups as $R^7$ but blocking groups may have been introduced in conventional manner.

Each of $M^1$ and $M^2$ may themselves be a mixture of two or more of the defined metals. $M^1$ is preferably magnesium or calcium. The preferred alcoholates are those in which $M^1$ is magnesium and $M^2$ is titanium or, less preferably, zirconium.

The novel alcoholates may be used in ester interchange processes either as a catalytic component or, preferably, as a reactant that supplies alkoxy groups during the process or as both. A process according to this aspect of the invention is one in which a compound $R^3COOR^4$ is made by ester interchange with a compound of the formula $R^3COOR^1$ in the presence of an alcoholate derived from an alcohol $R^4OH$ and, optionally, in the presence also of the alcohol $R^4OH$, wherein $R^1$ is $C_{1-3}$ alkyl, $R^3$ is an optionally substituted hydrocarbon, generally aliphatic hydrocarbon, group and $R^4$ is as defined above, and is characterised in that the alcoholate is present as a solution in the reaction mixture and is a mixed alcoholate of formula I above.

The alcoholate is generally formed before its introduction into the ester interchange reaction mixture but it may be formed within the reaction mixture. For instance, either or both of the metal alcoholate components may be formed within the reaction mixture, for instance by reaction of alcohol $R^4OH$ with metals $M^1$ and/or $M^2$ or compounds thereof. It appears possible that processes in which the mixed metal alcoholate contributes groups $OR^4$ to the reaction mixture can be regarded as processes in which the magnesium, calcium or barium component of the alcoholate contributes these groups for ester interchange with the starting ester $R^3COOR^1$ whilst the alcoholate of titanium, zirconium or aluminium reacts with the resultant magnesium, calcium or barium alcoholate, typically of the formula $M^1(OR^1)_2$, to reform the desired component $M^1(OR^4)_2$. This aspect of the invention therefore includes any ester interchange process conducted in the presence of an alcoholate of formula I irrespective of whether the alcoholate is a physical mixture of alcoholates of individual metals or whether it is a combined alcoholate containing both metals, and irrespective of how the combined alcoholate, or the individual components of a physical mixture of the alcoholates, has been provided into the reaction mixture.

The process is of particular value in the production of vinyl esters, and in particular in processes wherein $R^3$ is $CH_2=CH-$ or $CH_2=C(C_3)-$. $R^1$ is generally methyl so that the starting ester is preferably methyl acrylate or methacrylate but other suitable starting esters include ethyl acrylate and methacrylate.

The reaction is generally conducted in the absence of water.

The reaction may be conducted in the presence of alcohol $R^4OH$ to contribute some or all of the groups $OR^4$ in the final ester and so the alcoholate of formula I may be present in such processes solely or primarily as a catalyst and may be present in catalytic amounts. Preferably, however, the ester interchange process is conducted in the absence of water or reactive alcohol and the mixed metal alcoholate of formula I provides all the groups $OR^4$ in the final ester and this is of particular value when $R^3$ is an unsaturated group as defined above as there is a tendency for alcohol to add across the double bond and to form unwanted by-products. The preferred process is therefore a process broadly as described above but modified by the use of the defined alcoholate.

In such processes, the alcoholate may be present in molar excess, based on the starting ester, but the reaction is preferably conducted using an excess of the starting ester, for example 1.0 to 10 moles of ester per mol of alcoholate. The reaction mixture should be free of the starting alcohol or of any other alcohol that could react under the prevailing process conditions, and is generally free of any alcohol. The reaction mixture should be substantially anhydrous. Very small amounts of water or alcohol may be tolerated but even these may lead to some by-product formation.

The ester interchange processes of the invention may be carried out simply by mixing the starting ester with the chosen alcoholate. The reaction can be conducted at temperatures as high as 95° C. but best results are achieved at temperatures below 60° C., for instance 10°–50° C. Generally the reaction is conducted at from 20°–40° C., typically around 30° C.

The reaction is allowed to proceed towards, and often reach, equilibrium. During the process some or all of the groups $OR^4$ is the alcoholate are replaced by groups $OR^1$. The time required to reach final equilibrium depends upon the metal alcoholate and the reaction temperature but is generally 10 minutes to 2 hours. It is normally similar to the time required to reach equilibrium when the metal alcoholate is formed solely from metal $M^1$ and so is often in the range 30 to 75 minutes or less.

The process may be conducted batchwise with the desired ester and the resultant metal alcoholate being separated at the end of each batch but preferably the process is conducted continuously with the separation being conducted continuously during the process.

A preferred process of the invention is a cyclic process for making vinyl ester and in which metal alcoholate formed by ester interchange in the reaction mixture is separated from the reaction mixture and is reacted with excess alcohol $R^4OH$ in the substantial absence of ester $R^3COOR^1$ and the resultant metal alcoholate of formula I is recycled to the reaction mixture. This process has the advantage of achieving substantially total reuse of the metal whilst avoiding formation of azeotropes between the starting ester and the alcohol $R^1OH$.

The preferred process of the invention involves carrying out the following sequential steps. In step A, the ester interchange reaction is conducted between the metal alcoholate formed from the alcohol $R^4OH$ and an excess of the ester $R^3COOR^1$ to form a mixture containing the ester $R^3COOR^4$, unreacted ester $R^3COOR^1$ and metal alcoholate that has at least partially been converted to an alcoholate formed from the alcohol $R^1OH$. In step B, this alcoholate is separated from the reaction mixture, the ester $R^3COOR^4$ is recovered from the reaction mixture and the ester $R^3COOR^1$ is recycled for use in step A. In step C, the separated alcoholate from step B is reacted, in the substantial absence of ester $R^3COOR^1$, with excess alcohol $R^4OH$ to form alcohol $R^1OH$ and alcholate formed from the alcohol $R^4OH$. In step D, this alcoholate, formed in step C, is separated and recycled for use in step A and the alcohol $R^4OH$ is recovered and recycled for use in step C. The alcohol $R^1OH$ is taken off as an end product.

Generally step B is effected by separating the alcoholate from the esters followed by separating the esters by fractional distillation, while step C is effected by separating the alcoholate from the alcohols followed by separating the alcohols by fractional distillation.

The separation of the metal alcoholate from the reaction mixture is generally achieved by evaporation of the more volatile organic components from the less volatile metal alcoholate. In order to avoid prolonged heating, this evaporation is preferably by flash evaporation. The separated alcoholate is a compound of formula I. If the reaction with alcohol $R^4OH$ has been complete, the compound will be free of groups $R^7$ that are lower alkoxy groups (although it may include blocking groups $R^7$) but if the reaction has been incomplete the recycled metal alcoholate will include some lower alkoxy groups $R^7$.

The processes described above (give high yield of desired product, low impurities, low usage of metal alcoholate and easier separation procedures than prior art processes) together with major additional advantages.

Because of the stability of the metal alkoxide and of vinyl ester with which it is in contact, it is possible to store the regenerated mixed metal alkoxide of the invention diluted with the starting methyl acrylate or other ester at convenient low temperatures without incurring the risk of metal alkoxide polymerisation. The process can be operated at lower temperatures, as a homogeneous system, but at reactivity rates similar to or better than those previously attainable only in heterogeneous systems or at much higher temperatures in homogeneous systems. The metal alcoholate can be reused for much longer periods than were possible in the prior process without unacceptable build-up of by-products, increase in difficulties of separation, or loss of activity. The risk of polymerisation of methylacrylate or other vinyl ester in the homogeneous reaction mixture is reduced. The difficulties of separation and recycling associated with prior heterogeneous systems, and the risk of the formation of titanium based polymers in prior homogeneous systems, is reduced or eliminated.

The following are some examples.

EXAMPLE 11

A catalyst of formula I wherein $M^1$ is Mg, $M^2$ is Ti, a and b are zero, x is 0.05 and $R^4$ is dimethylaminoethyl is made by reacting excess dimethylaminoethanol (DMAE) with a 5:95 molar mixture of magnesium diisopropoxide and titanium tetra-isopropoxide. The reaction is conducted by heating the alcohol with the isopropoxides in a stirred reactor with a fractionation column and reflux splitter. Isopropanol is removed at the top of the column and vacuum is applied at the end of the reaction to remove the last traces of isopropanol. The reactor contains the desired alcoholate of formula I as a mobile liquid having no sign of precipitate. Analysis shows the product to be free of alcohol and isopropoxide groups and to have to have the molar analysis Mg=0.05, Ti=0.95, dimethylaminoethoxy=3.9, corresponding to the formula

$$[Mg(DMAE)_2]_{0.05}[Ti(DMAE)_4]_{0.95}$$

In a similar manner, it is possible to form the corresponding alcoholates of, for instance, calcium and titanium, magnesium and zirconium, magnesium and aluminium, and barium and titanium. In a similar manner, it is possible to form magnesium titanium, and other metal, alcoholates having values of x up to 0.5.

In a similar manner, it is possible to form alcoholates when $R^4$ is, for instance, 2-ethylhexyl or other higher alkyl or cycloalkyl group.

Alcoholates containing a blocking group $R^7$ may be made by starting with, for instance, titanium $C_{18}$ alkoxide triisopropoxide, instead of titanium tetraisopropoxide.

EXAMPLE 12

300 grams of metal alcoholate is reacted with 344 grams of methylacrylate at varying temperatures. The alcohol is DMAE. The molar ratio of methylacrylate to the dimethylaminoethanol ligand (DMAE) is 4:3. The formation of dimethylaminoethyl acrylate (DMAEA) is monitored by Gas Chromatography throughout the reaction. The results are then plotted assuming pseudo first order kinetics and the rate constant obtained. The higher the rate constant, the more rapid the reaction.

The reaction is conducted twice at each temperature. In reaction series A, the metal alcoholate is Ti(DMAE)$_4$. In series B, the metal alcoholate is the titanium magnesium alcoholate whose analysis and manufacture is given in Example 11. The results are shown in Table 5.

TABLE 5

| Temperature (°C.) | Rate Constant (min$^{-1}$) × 10$^2$ | |
|---|---|---|
|  | A | B |
| 30 | — | 3.57 |
| 40 | — | 5.25 |
| 50 | 1.775 | 6.73 |
| 60 | 3.399 | 7.3 |
| 70 | 5.536 | 9.75 |
| 80 | 9.75 | — |
| 90 | 14.2 | — |

This shows the Mg/Ti reagent to result in a much more rapid rate of reaction than the titanium alone at the same temperature. The Mg/Ti compound is capable of inducing reaction to DMAEA even at temperatures as low as 30° C.

A similar clear trend is observed when comparisons are made between Ti and Ti$_{0.95}$ Ca$_{0.05}$, Zr and Zr$_{0.95}$ Mg$_{0.05}$, Al and Al$_{0.95}$ Mg$_{0.05}$. A similar trend is observed when the alcohol is 2-ethylhexanol instead of DMAE.

EXAMPLE 13

Using a molar ratio of 5/3 methyl acrylate to dimethylaminoethyl ligand, the rates of reaction of Ti(DMAE)$_4$ versus the Ti Mg alcoholate made in Example 11 are determined at room temperature (20° C.) by measuring the percentage of DMAEA in the reaction mixture after various reaction times in two reactions. In Reaction B, 30 g of the mixed alcoholate is reacted with 43 g methyl acrylate. In Reaction A, 50 g Ti(DMAE)$_4$ is reacted with 71.6 g methyl acrylate.

TABLE 6

| Time (mins) | Reaction A | Reaction B |
|---|---|---|
| 1 | 0 | 8.9 |
| 5 | 0 | 15.8 |
| 10 | 0.9 | 19.0 |
| 30 | 2.4 | 21.5 |
| 45 | 3.7 | 22.2 |
| 60 | 5.0 | 21.5 |

This shows the faster rate of reaction using magnesium and titanium compared to the use of titanium alone.

EXAMPLE 14

3:1 mole ratio mixtures of methylacrylate (MA) and dimethylaminoethanol (DMAE) are reacted together at 40° C. in the presence of (A) Ti(DMAE)$_4$ and (B) Ti$_{0.5}$ Mg$_{0.5}$(DMAE)$_3$ at a level of 2.6 mole percent catalyst based on DMAE.

Samples of the mixtures are taken at intervals and the mole % conversion of DMAE to DMAEA was recorded. The results obtained are as follows:

TABLE 7

| TIME (mins) | A | B |
|---|---|---|
| 0 | — | — |
| 10 | 1.0 | 38.8 |
| 25 | — | 52.9 |
| 35 | 3.5 | 57.9 |
| 50 | — | 63.0 |
| 80 | 6.5 | 66.1 |

This clearly demonstrates the advantage of catalyst according to the invention in an ester interchange conducted using a reactive alcohol.

EXAMPLE 15

In reaction A, 87.2 g of Zr(DMAE)$_4$ are weighed into a 3-neck round bottom flask fitted with a stirrer and placed in a water bath held at 40° C. 112.8 g MA are added (molar ratio MA:DMAE=5:3). The time is noted as time zero and samples of the reaction mixture are taken at varying times thereafter and analysed by GLC to determine the percentage DMAEA in the reaction mixture. In series B, the process is repeated except that the alcoholate is Zr$_{0.95}$ Mg$_{0.05}$ (DMAE)$_{3.9}$. The results are shown in Table 8.

TABLE 8

| Reaction Time (mins) | A | B |
|---|---|---|
| 5 | 2.5 | 4.5 |
| 10 | 4.9 | 6.8 |
| 15 | 8.1 | 12.3 |
| 20 | 11.2 | 14.2 |
| 25 | 13.5 | 19.3 |
| 30 | 15.1 | 20.4 |
| 45 | 22.5 | 28.7 |
| 60 | 26.4 | 30.2 |

This shows that the incorporation of a small amount of magnesium gives a significant improvement in the rate of formation of DMAEA.

EXAMPLE 16

To demonstrate the effect of varying the proportions of titanium and magnesium in the metal alcoholate, a series of reactions as in Example 12 are conducted and the percentage DMAEA in the reaction mixture is recorded at 5, 30, 60 and above 180 minutes from the start of the reaction. The results are shown in Table 9.

TABLE 9

| Reaction Time | 100 Ti 0 Mg | 95 Ti 5 Mg | 90 Ti 10 Mg | 80 Ti 20 Mg | 50 Ti 50 Mg | 0 Ti 100 Mg |
|---|---|---|---|---|---|---|
| 5 | 0 | 2.2 | 3.8 | 7.5 | (16) | 7.7 |
| 30 | 2.4 | (10) | 9.1 | 14.3 | 24.5 | 19.5 |
| 60 | 5.0 | 17.2 | (12) | 16.8 | 25.1 | (23) |
| >180 | 24.0 | 26.5 | 25.2 | 27.8 | 25 | 27.5 |

The values in parenthesis are obtained by interpolation.

EXAMPLE 17

5 moles methylacrylate are reacted with 1 mole of the titanium magnesium alcoholate made and analysed in Example 11. The reactants are charged to a reaction vessel maintained at about 40° C. Equilibrium is obtained after about 60 minutes and the volatiles (including DMAEA) are removed by rapid distillation at 120° C. and 20 mm Hg leaving a liquid residue. The DMAEA that is separated from the volatiles is found to be substantially pure. The liquid residue is regenerated with 1 to 2 moles DMAE per mole of methoxide in the residue and methanol and DMAE are removed slowly by distillation on a rotary evaporator. The residue is recycled for further reaction with methylacrylate.

I claim:

1. A process in which a compound $R^3COOR^4$ is made by ester interchange with a compound $R^3COOR^1$ in the presence of an alcoholate derived from an alcohol $R^4OH$ and optionally in the presence also of the alcohol $R^4OH$, wherein $R^1$ is $C_{1-3}$ alkyl, $R^3$ is $CH_2=CH-$ or $CH_2=C(CH_3)$ and $R^4$ is selected from alkyl having at least 4 carbon atoms, cycloalkyl having at least 4 carbon atoms and aminoalkyl, characterised in that the alcoholate is present as a solution in the reaction mixture and has the empirical formula $$[M^1(OR^4)_{2-a}R_a^7]_x[M^2(OR^4)_{n-b}R_b^7]_y \qquad I$$

wherein
 $M^1$ is selected from Mg, Ca and Ba
 $M^2$ is selected from Ti, Zr and Al
 n is 3 or 4 and is the valency of $M^2$
 a is a number from 0 to 1.5
 b is a number from 0 to 0.75n
 $x+y=1$ and each is a number from 0.005 to 0.995 and is such that the compound is liquid at 30° C.
 $R^4$ is as defined above and
 each group $R^7$ is individually selected from (a) $C_{1-3}$ alkoxy groups and (b) $C_{8-30}$ alkyl or alkoxy blocking groups that are substantially less reactive in the ester interchange reaction than the groups $OR^4$.

2. A process according to claim 1 conducted in the presence of the alcohol $R^4OH$ and wherein the alcoholate serves as a catalyst.

3. A process according to claim 1 wherein $R^3$ is $CH_2=CH-$ or $CH_2=C(CH_3)-$, the process is conducted in the absence of reactive alcohol and the metal alcoholate provides the groups $OR^4$ that are utilised in forming the desired ester and reacts with the compound $R^3COOR^1$.

4. A process according to claim 1 wherein $R^3$ is $CH_2=CH-$ or $CH_2=C(CH_3)-$, the process is conducted in the absence of reactive alcohol and the metal alcoholate provides the groups $OR^4$ that are utilised in forming the desired ester and reacts with the compound $R^3COOR^1$ and the metal alcoholate formed in the reaction mixture is separated from the reaction mixture and is reacted with excess alcohol $R^4OH$ in the substantial absence of ester $R^3COOR^1$ and the resultant metal alcoholate of formula I is recycled to the reaction mixture.

5. A process according to claim 4 in which the separation of the metal alcoholate is by evaporation of the esters in the reaction mixture from the metal alcoholate.

6. A process according to claim 1 conducted in the absence of an inert solvent.

7. A process according to claim 1 in which at the start of the process, a and b in the metal alcoholate are both zero.

8. A process according to claim 1 in which $M^1$ is Mg and $M^2$ is selected from Ti and Zr.

9. A process according to claim 1 in which x is 0.01 to 0.5, preferably 0.02 to 0.2.

10. A process according to claim 1 in which $R^4$ is selected from $C_{5-30}$ alkyl, $C_{5-8}$ cycloalkyl and dialkylaminoalkyl of the formula $(R^5)_2N-C_nH_{2n}$ wherein n is 2 or 3 and the groups $R^5$ are the same or different and are $C_{1-3}$ alkyl.

* * * * *